(12) United States Patent
Huang et al.

(10) Patent No.: US 12,322,506 B2
(45) Date of Patent: Jun. 3, 2025

(54) DISCRIMINATION DEVICE, DISCRIMINATION METHOD, AND PROGRAM RECORDING MEDIUM

(71) Applicant: NEC Corporation, Tokyo (JP)

(72) Inventors: Chenhui Huang, Tokyo (JP); Kazuki Ihara, Tokyo (JP); Noriyuki Tonouchi, Tokyo (JP); Kenichiro Fukushi, Tokyo (JP)

(73) Assignee: NEC CORPORATION, Tokyo (JP)

( * ) Notice: Subject to any disclaimer, the term of this patent is extended or adjusted under 35 U.S.C. 154(b) by 790 days.

(21) Appl. No.: 17/599,031

(22) PCT Filed: Apr. 1, 2019

(86) PCT No.: PCT/JP2019/014489
§ 371 (c)(1),
(2) Date: Sep. 28, 2021

(87) PCT Pub. No.: WO2020/202437
PCT Pub. Date: Oct. 8, 2020

(65) Prior Publication Data
US 2022/0181016 A1  Jun. 9, 2022

(51) Int. Cl.
*G16H 40/63* (2018.01)
*A61B 5/00* (2006.01)
(Continued)

(52) U.S. Cl.
CPC ........... *G16H 40/63* (2018.01); *A61B 5/1123* (2013.01); *A61B 5/6807* (2013.01); *G01P 15/00* (2013.01);
(Continued)

(58) Field of Classification Search
CPC ..... G01P 15/00; A61B 5/1123; A61B 5/6807; A61B 5/112; A61B 2560/0209; A61B 5/11

See application file for complete search history.

(56) References Cited

U.S. PATENT DOCUMENTS

| 6,898,550 B1 * | 5/2005 | Blackadar | A43B 3/0031 702/182 |
| 2011/0140890 A1 * | 6/2011 | Vock | A43B 3/50 340/540 |
| 2016/0166880 A1 | 6/2016 | Nakajima | |

FOREIGN PATENT DOCUMENTS

| JP | 2016-112108 A | 6/2016 |
| JP | 2017-217213 A | 12/2017 |
| JP | 2018-047261 A | 3/2018 |

OTHER PUBLICATIONS

International Search Report for PCT Application No. PCT/JP2019/014489, mailed on Jun. 25, 2019.
(Continued)

*Primary Examiner* — Matthew G Marini
*Assistant Examiner* — Leo T Hinze
(74) *Attorney, Agent, or Firm* — Sughrue Mion, PLLC

(57) ABSTRACT

A discrimination device includes: a log acquisition unit that acquires sensor data including acceleration acquired by a sensor placed in a shoe, a storage unit that stores log data of the sensor data, a log calling unit that calls the log data stored in the storage unit, a discrimination unit that distinguishes a walking state from a waveform of the log data, a threshold setting unit that retains a first threshold and a second threshold, and sets the first threshold and the second threshold based on a discrimination result, and a transmission unit that transmits the discrimination result. When acceleration in the log data has not exceeded the second threshold within a discrimination time, the discrimination (Continued)

device outputs a discrimination result of being erroneous activation, and updates the first threshold based on a value of the acceleration in the traveling direction in the log data according to the discrimination result.

10 Claims, 10 Drawing Sheets

(51) Int. Cl.
*A61B 5/11* (2006.01)
*G01P 15/00* (2006.01)

(52) U.S. Cl.
CPC ....... *A61B 5/112* (2013.01); *A61B 2560/0209* (2013.01)

(56) References Cited

OTHER PUBLICATIONS

English translation of Written opinion for PCT Application No. PCT/JP2019/014489, mailed on Jun. 25, 2019.

\* cited by examiner

DISCRIMINATION DEVICE, DISCRIMINATION METHOD, AND PROGRAM RECORDING MEDIUM

This application is a National Stage Entry of PCT/JP2019/014489 filed on Apr. 1, 2019, the contents of all of which are incorporated herein by reference, in their entirety.

TECHNICAL FIELD

The present invention relates to a discrimination device, a discrimination method, and a program for distinguishing a walking state.

BACKGROUND ART

In response to growing interest in healthcare for physical condition management, a technique has been developed for measuring walking using sensor data acquired by a sensor attached to a body. In order to stably use the walking measurement for a long time, power saving of a sensor that acquires sensor data and a measurement device that performs walking measurement using the sensor data is required.

PTL 1 discloses a walking-linked communication device that performs communication in conjunction with walking of a user. The device of PTL 1 includes a pressure sensing unit that detects a foot pressure of the user during walking or running, a communication unit that transmits data, and a control unit that controls the pressure sensing unit and the communication unit. The control unit of the device of PTL 1 monitors output of the pressure sensing unit and controls on and off of transmission of data by the communication unit according to the relationship between the output and a threshold.

CITATION LIST

Patent Literature

[PTL 1] JP 2017-217213 A

SUMMARY OF INVENTION

Technical Problem

According to the method of PTL 1, power consumption at the time of transmission of data by the communication unit can be suppressed. However, in the method of PTL 1, because the threshold set for output of the pressure sensing unit is fixed, there is a problem that it is difficult to cope with a change when the use environment of the user changes. For example, the device of PTL 1 may not be activated or may be erroneously activated depending on setting of the threshold. The method of PTL 1 has a problem that, due to a change in the walking state, the threshold is too high and measurement efficiency deteriorates, or the threshold is too low and the power is excessively consumed.

An object of the present invention is to solve the above-described problems, and to provide a discrimination device that achieves high efficiency and low power consumption of walking measurement while flexibly responding to changes in a walking state.

Solution to Problem

A discrimination device according to one aspect of the present invention includes a log acquisition unit that acquires sensor data including acceleration acquired by a sensor placed in a shoe, a storage unit that stories log data of the sensor data acquired by the log acquisition unit, a log calling unit that calls the log data stored in the storage unit, a discrimination unit that distinguishes a walking state from a waveform of the log data called by the log calling unit, a threshold setting unit that retains a first threshold related to acceleration in a gravity direction and a second threshold related to acceleration in a traveling direction, and sets the first threshold and the second threshold based on a discrimination result by the discrimination unit, and a transmission unit that transmits the discrimination result by the discrimination unit. When acceleration included in the log data has not exceeded the second threshold within a discrimination time, the discrimination unit outputs a discrimination result that it is erroneous activation. The threshold setting unit updates the first threshold based on a value of the acceleration in the traveling direction included in the log data according to the discrimination result that it is erroneous activation.

A discrimination method of one aspect of the present invention includes acquiring sensor data including acceleration acquired by a sensor placed in a shoe, storing log data of the acquired sensor data in a storage unit, calling the log data stored in the storage unit, distinguishing a walking state from a waveform of the called log data, setting a first threshold related to acceleration in a gravity direction and a second threshold related to acceleration in a traveling direction based on a discrimination result of the walking state, outputting a discrimination result that it is erroneous activation when acceleration included in the log data has not exceeded the second threshold within a discrimination time, and updating the first threshold based on a value of the acceleration in the traveling direction included in the log data according to the discrimination result that it is erroneous activation.

A program according to one aspect of the present invention causes a computer to execute processing including acquiring sensor data including acceleration acquired by a sensor placed in a shoe, storing the log data of the acquired sensor data in a storage unit, calling the log data stored in the storage unit, distinguishing a walking state from a waveform of the called log data, setting a first threshold related to acceleration in a gravity direction and a second threshold related to acceleration in a traveling direction based on a discrimination result of the walking state, outputting a discrimination result that it is erroneous activation when acceleration included in the log data has not exceeded the second threshold within a discrimination time, and updating the first threshold based on a value of the acceleration in the traveling direction included in the log data according to the discrimination result that it is erroneous activation.

Advantageous Effects of Invention

According to the present invention, it is possible to provide a walking discrimination device that achieves high efficiency and low power consumption of walking measurement while flexibly responding to changes in a walking state.

EXAMPLE EMBODIMENT

Figure 1:
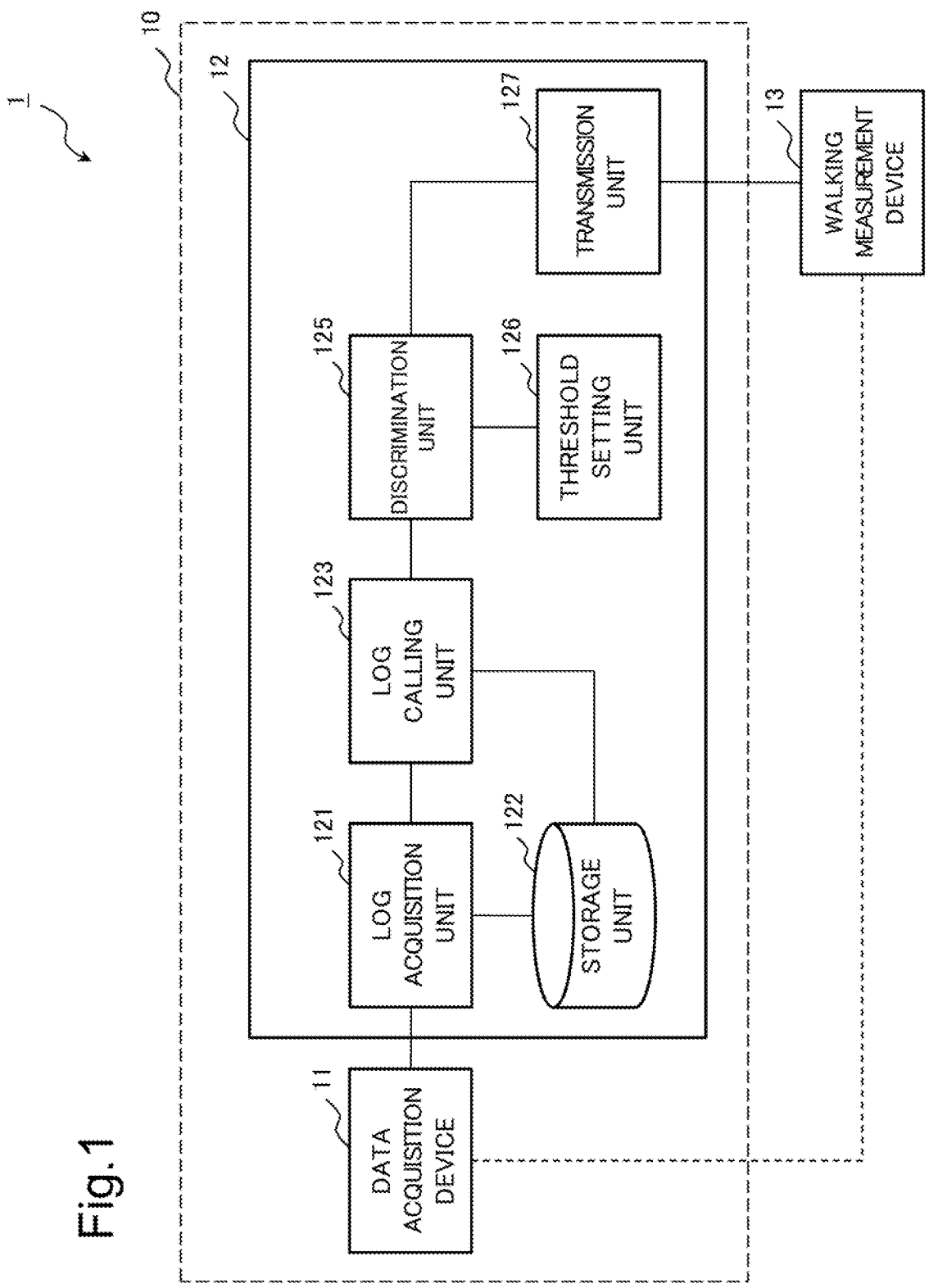
FIG. 1 is a block diagram illustrating a configuration of a walking measurement system according to a first example embodiment of the present invention.

Hereinafter, example embodiments of the present invention will be described with reference to the drawings. However, although the example embodiments to be described below are technically preferably limited in order to carry out the present invention, the scope of the invention is not limited to the following. In all the drawings used in the following description of the example embodiment, the same reference numerals are given to similar parts unless there is a particular reason. In the following example embodiments, repeated description of similar configurations and operations may be omitted. The directions of arrows in the drawings illustrate examples, and do not limit the directions of signals and processing between blocks.

First Example Embodiment

First, a walking measurement system according to a first example embodiment of the present invention will be described with reference to the drawings. The walking measurement system of the present example embodiment calculates an attitude angle using sensor data acquired by an acceleration sensor and an angular velocity sensor arranged on a shoe, and measures walking on the basis of time series data of the attitude angle. For example, the walking measurement system of the present example embodiment calculates the attitude angle using acceleration data and angular velocity data acquired by an inertial measurement unit (IMU) arranged on a shoe footbed (also referred to as an insole). When switching an operation mode using the sensor data, the walking measurement system of the present example embodiment distinguishes the walking state using the acceleration data acquired by the acceleration sensor, and performs walking measurement according to the discrimination result.

(Configuration)

FIG. 1 is a block diagram illustrating an example of a configuration of a walking measurement system 1 of the present example embodiment. The walking measurement system 1 includes a data acquisition device 11, a discrimination device 12, and a walking measurement device 13. The data acquisition device 11 and the discrimination device 12 constitute a walking discrimination device 10. The data acquisition device 11 and the discrimination device 12 may be connected by wire or wirelessly. The discrimination device 12 and the walking measurement device 13 may be connected by wire or wirelessly. A display device (not illustrated) that displays a discrimination result of the discrimination device 12 and a measurement result of the walking measurement device 13 may be added to the walking measurement device 13. When the walking measurement device 13 includes a display unit, the discrimination result of the discrimination device 12 and the measurement result of the walking measurement device 13 may be displayed on the display unit of the walking measurement device 13.

Figure 2:
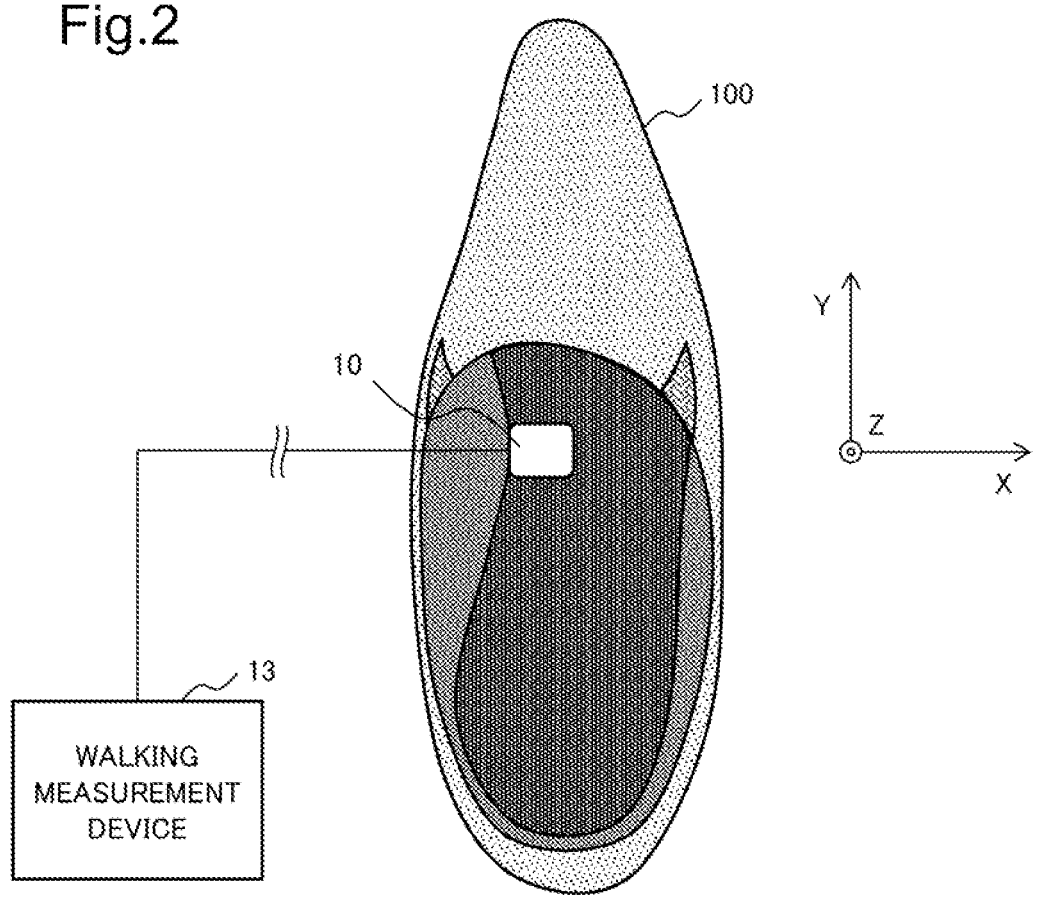
FIG. 2 is a conceptual diagram illustrating an arrangement example of a walking discrimination device of the walking measurement system according to the first example embodiment of the present invention.

FIG. 2 is a conceptual diagram illustrating an example in which the walking discrimination device 10 is installed in the shoe 100. In the example of FIG. 2, the walking discrimination device 10 is installed at a position corresponding to a back side of an arch of the foot. The position where the walking discrimination device 10 is installed may be a position other than the back side of the arch of the foot as long as it is in the shoe or on a surface of the shoe. For example, the walking discrimination device 10 is installed on an insole inserted into the shoe 100. The walking discrimination device 10 may be installed in footwear other than shoes, socks, or the like as long as a walking state can be detected.

The data acquisition device 11 is connected to the discrimination device 12. The data acquisition device 11 includes at least an acceleration sensor and an angular velocity sensor. The data acquisition device 11 converts data acquired by the acceleration sensor and the angular velocity sensor into digital data (also referred to as sensor data), and transmits the sensor data after the conversion to the discrimination device 12. The data acquisition device 11 and the walking measurement device 13 may be configured to be directly connected without interposing the discrimination device 12 therebetween.

Figure 3:
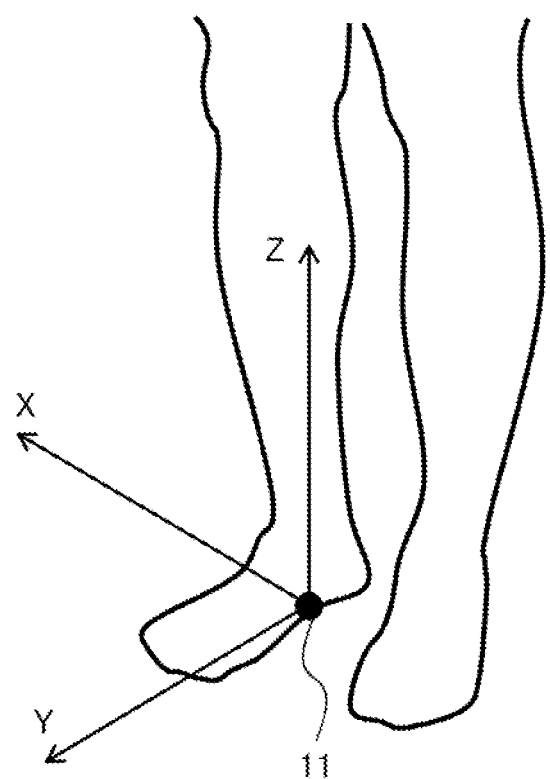
FIG. 3 is a conceptual diagram for illustrating a coordinate system of sensor data acquired by the walking measurement system according to the first example embodiment of the present invention.

FIG. 3 is a conceptual diagram for illustrating a coordinate system of sensor data acquired by the data acquisition device 11. In the example of FIG. 3, a lateral direction of a walker is set to an X-axis direction (rightward direction is positive), a traveling direction of the walker is set to a Y-axis direction (forward direction is positive), and a gravity direction is set to a Z-axis direction (vertically upward direction is positive).

The data acquisition device 11 is achieved by, for example, an inertial measurement device including an acceleration sensor and an angular velocity sensor. An example of the inertial measurement device is the IMU. The IMU includes a three-axis acceleration sensor and an angular velocity sensor. An example of the inertial measurement device is a vertical gyro (VG). The VG has a configuration similar to that of the IMU, and can output a roll angle and a pitch angle with reference to the gravity direction by a method called strapdown. An example of the inertial measurement device is an attitude heading reference system (AHRS). The AHRS has a configuration in which an electronic compass is added to the VG. The AHRS can output a yaw angle in addition to the roll angle and the pitch angle. As an example of the inertial measurement device, there is a global positioning system/inertial navigation system (GPS/INS). The GPS/INS has a configuration in which the GPS is added to the AHRS. The GPS/INS can calculate a position in a three-dimensional space in addition to an attitude angle (roll angle, pitch angle, and yaw angle), the position can be estimated with high accuracy.

When the acceleration data is used, the attitude angle can be calculated from the magnitude of acceleration applied in the axial direction of each of the pitch axis and the roll axis. When the angular velocity data is used, values of the angular velocity with each of the pitch axis, the roll axis, and the yaw axis as central axes can be integrated, to thereby calculate the attitude angle around each of these axes. Meanwhile, high frequency noise changing in various directions is included in the acceleration data, and low frequency noise in the same direction is always included in the angular velocity data. Thus, by applying a low-pass filter to the acceleration data to remove a high-frequency component, applying a high-pass filter to the angular velocity data to remove a low-frequency component, and combining outputs thereof, accuracy of sensor data from a foot portion in which noise is easily mixed is improved. It is also possible to improve accuracy of the sensor data by applying a complementary filter to each of the acceleration data and the angular velocity data and taking a weighted average.

The discrimination device 12 is connected to the data acquisition device 11 and the walking measurement device 13. The discrimination device 12 acquires sensor data from the data acquisition device 11. For example, the discrimination device 12 is achieved by a microcomputer.

The discrimination device 12 switches the operation mode of the walking measurement system 1 according to a value of the acceleration data included in the sensor data from the data acquisition device 11. The walking measurement system 1 operates in at least two operation modes including a power saving mode and a normal mode. The power saving mode is a mode in which the discrimination device 12 operates and the walking measurement device 13 stops. The normal mode is a mode in which the discrimination device 12 operates in a walking discrimination phase and the walking measurement device 13 operates normally. For example, in order to reduce the power consumption of the walking discrimination device 10, the discrimination device 12 may be configured such that an acquisition frequency and a discrimination frequency of data are reduced in the power saving mode, and the acquisition frequency and the discrimination frequency of data are increased in the walking discrimination phase of the normal mode.

The discrimination device 12 switches the operation mode using two thresholds. A first threshold of the two thresholds is a threshold set for acceleration in the gravity direction (Z direction in FIG. 3) when the operation mode is switched from the power saving mode to the normal mode. A second threshold of the two thresholds is a threshold set for acceleration in the traveling direction (Y direction in FIG. 3) during the walking discrimination phase for several seconds after switching from the operation mode to the normal mode.

When the acceleration in the gravity direction (Z direction in FIG. 3) exceeds the first threshold, the discrimination device 12 switches from the power saving mode to the normal mode. When switching from the power saving mode to the normal mode, the discrimination device 12 transmits the sensor data to the walking measurement device 13. The walking measurement device 13 that has received the sensor data from the discrimination device 12 shifts to the normal mode with the sensor data as a trigger. When switching from the power saving mode to the normal mode, a trigger signal may be transmitted from the discrimination device 12 to the walking measurement device 13, and the walking measurement device 13 responding to the trigger signal may be configured to directly receive the sensor signal from the data acquisition device 11.

The discrimination device 12 verifies whether the acceleration in the traveling direction exceeds the second threshold using log data (hereinafter also referred to as a log) of the sensor data in the walking discrimination phase immediately after switching to the normal mode. The discrimination device 12 distinguishes whether it is stable walking, stop of walking, or erroneous activation according to a verification result of whether the acceleration in the traveling direction exceeds the second threshold.

When the discrimination device 12 distinguishes that it is stable walking, the discrimination device 12 continues transmitting the sensor data to the walking discrimination device 10. By continuing the transmission of the sensor data from the discrimination device 12 to the walking measurement device 13, the walking measurement by the walking measurement device 13 is performed in the normal mode. When the walking measurement device 13 is configured to directly receive the sensor signal from the data acquisition device 11, it is only required to transmit a trigger signal indicating a discrimination result that it is stable walking from the discrimination device 12 to the walking measurement device 13. In that case, the walking measurement by the walking measurement device 13 is continued according to the trigger signal. The walking measurement by the walking measurement device 13 may be configured to be continued unless the trigger signal is received from the discrimination device 12.

When the discrimination device 12 distinguishes that walking is stopped, the discrimination device 12 stops transmitting the sensor data to the walking measurement device 13. By stopping the transmission of the sensor data from the discrimination device 12 to the walking measurement device 13, the walking measurement by the walking measurement device 13 is stopped. When the walking measurement device 13 is configured to directly receive the sensor signal from the data acquisition device 11, it is only required to transmit a trigger signal indicating a discrimination result that walking is stopped from the discrimination device 12 to the walking measurement device 13. In that case, the walking measurement by the walking measurement device 13 is stopped according to the trigger signal.

When the discrimination device 12 distinguishes that it is erroneous activation, the discrimination device 12 updates the first threshold on the basis of a maximum value of the acceleration in the traveling direction (Y direction in FIG. 3), and the transmission of the sensor data to the walking measurement device 13 is stopped. By stopping the transmission of the sensor data from the discrimination device 12 to the walking measurement device 13, the walking measurement by the walking measurement device 13 is stopped. If the first threshold is updated to an excessively large value, there is a possibility that the discrimination device 12 will not be activated thereafter. Therefore, when the discrimination device 12 is not activated even once under a certain condition (for example, several hours), the value of the first threshold is returned to a value at the time of a previous normal activation. When the walking measurement device 13 is configured to directly receive the sensor signal from the data acquisition device 11, it is only required to transmit a signal indicating a discrimination result that it is erroneous activation from the discrimination device 12 to the walking measurement device 13. In that case, the walking measurement by the walking measurement device 13 is stopped in response to the signal indicating the discrimination result that it is erroneous activation.

The walking measurement device 13 receives sensor data from the data acquisition device 11 via the discrimination device 12. The walking measurement device 13 executes the walking measurement using the received sensor data. Note that in the present example embodiment, the configuration and operation of the walking measurement device 13 are not particularly limited as long as the walking measurement is executed using the sensor data. The walking measurement device 13 may be configured to directly receive the sensor signal from the data acquisition device 11 according to the trigger signal output when the discrimination device 12 shifts to the normal mode.

For example, the walking measurement device 13 calculates the attitude angle using the received sensor data. In the present example embodiment, the attitude angle is an angle of the sole surface with respect to a horizontal plane (ground). The walking measurement device 13 generates time series data of the attitude angle. The walking measurement device 13 generates the time series data of the attitude angle at a predetermined timing or a predetermined time interval set in accordance with a general walking cycle or a walking cycle unique to the user. The walking measurement device 13 executes walking measurement using the time series data of the attitude angle. The walking measurement device 13 outputs an analysis of a walking phase and measurement results of a stride, a walking speed, a sensor height, and the like to a display device that is not illustrated or another system.

The walking measurement device 13 acquires a discrimination result by the discrimination device 12. The walking measurement device 13 continues or stops the walking measurement on the basis of the discrimination result from the discrimination device 12. For example, the walking measurement device 13 continues to generate the time series data of the attitude angle in a period in which walking of the user is continued (stable walking period). The walking measurement device 13 performs the walking measurement using the generated time series data. The timing of generating the time series data of the attitude angle and contents of the walking measurement can be freely set.

For example, the walking measurement device 13 is achieved by software (application) or a circuit installed in a portable terminal device such as a smartphone, a mobile phone, a tablet, or a laptop personal computer. When the walking measurement device 13 is used for data analysis in research or the like, for example, the walking measurement device 13 may be achieved by software or a circuit installed in an information processing device such as a stationary computer or a server.

The configuration of the walking measurement system 1 has been described above. Note that the configuration of the walking measurement system 1 of FIG. 1 is an example, and the configuration of the walking measurement system 1 of the present example embodiment is not limited to the mode as it is.

[Assessment Device]

Next, a configuration of the discrimination device 12 will be described with reference to the drawings. As illustrated in FIG. 1, the discrimination device 12 includes a log acquisition unit 121, a storage unit 122, a log calling unit 123, a discrimination unit 125, a threshold setting unit 126, and a transmission unit 127. For example, the components of the discrimination device 12 may be achieved by a microcomputer having a dedicated circuit, or may be achieved by software mounted on the microcomputer.

The log acquisition unit 121 is connected to the data acquisition device 11, the storage unit 122, and the log calling unit 123. The log acquisition unit 121 receives the log data of the sensor data from the data acquisition device 11. The log acquisition unit 121 stores the received log data in the storage unit 122. The log acquisition unit 121 outputs a call instruction for the log data to the log calling unit 123. For example, every time the log data is acquired, the log acquisition unit 121 outputs the call instruction for the log data to the log calling unit 123. For example, the log acquisition unit 121 outputs the call instruction for the log data to the log calling unit 123 when a predetermined time elapses after acquisition of the log data. The timing at which the log acquisition unit 121 outputs the call instruction for the log data to the log calling unit 123 can be freely set. When the log calling unit 123 is configured to control the call for the log data, it is only required to configure the log acquisition unit 121 not to perform the call instruction for the log data to the log calling unit 123.

The storage unit 122 is connected to the log acquisition unit 121 and the log calling unit 123. In the storage unit 122, the log data of the sensor data is stored by the log acquisition unit 121. The storage unit 122 receives an access by the log calling unit 123, and the log data of the sensor data stored in itself is read by the log calling unit 123.

The log calling unit 123 is connected to the log acquisition unit 121, the storage unit 122, and the discrimination unit 125. The log calling unit 123 reads the log data of the sensor data from the storage unit 122 in response to the call instruction for the log from the log acquisition unit 121. The log calling unit 123 outputs the called log data to the discrimination unit 125. When the log calling unit 123 is configured to control the call for the log data, it is only required to set a timing at which the log data is called in the log calling unit 123. In this case, it is only required to configure the log calling unit 123 to read the log data at a predetermined timing set in advance or at predetermined time intervals.

The discrimination unit 125 is connected to the log calling unit 123, the threshold setting unit 126, and the transmission unit 127. The discrimination unit 125 acquires the log data of the sensor data from the log calling unit 123. The discrimination unit 125 switches the operation mode using two thresholds. A first threshold of the two thresholds is a threshold set for acceleration in the gravity direction (Z direction in FIG. 3) when it is switched from the power saving mode to the normal mode. A second threshold of the two thresholds is a threshold set for acceleration in the traveling direction (Y direction in FIG. 3) in the walking discrimination phase for several seconds after switching from the power saving mode to the normal mode.

If the acceleration in the gravity direction exceeds the first threshold, the discrimination unit 125 switches the operation mode from the power saving mode to the normal mode. After switching the operation mode to the normal mode, the discrimination unit 125 verifies whether the acceleration in the traveling direction exceeds the second threshold using the log data of the sensor data, thereby distinguishing whether it is stable walking, stop of walking, or erroneous activation.

When the acceleration in the traveling direction has exceeded the second threshold in a period until a predetermined discrimination time elapses, the discrimination unit 125 verifies whether the acceleration in the traveling direction has exceeded the second threshold by a prescribed number of times or more in the period until the discrimination time elapses. For example, the discrimination time is set to an elapsed time (about five seconds) of about several steps in general walking. For example, the prescribed number of times is set in accordance with the number of steps in an elapsed time of about several steps in general walking. When the elapsed time is set to five seconds and it is estimated that it is stable walking if the number of steps of about three to five steps is measured, it is only required to set the prescribed number of times to about three times. The discrimination time and the prescribed number of times may be set to initial setting values based on actual measurement values, or may be individually set for each user.

When the acceleration in the traveling direction has exceeded the second threshold by the prescribed number of times or more in the period until the discrimination time elapses, the discrimination unit 125 distinguishes that it is stable walking. In this case, the discrimination unit 125 outputs a discrimination result that it is stable walking to the transmission unit 127. On the other hand, when the acceleration in the traveling direction has not exceeded the second threshold by the prescribed number of times or more in the period until the discrimination time elapses, the discrimination unit 125 distinguishes that walking is stopped. In this case, the discrimination unit 125 outputs a discrimination result that walking is stopped to the transmission unit 127.

When the acceleration in the traveling direction has not exceeded the second threshold in the period until the predetermined discrimination time elapses, the discrimination unit 125 distinguishes that it is erroneous activation. When the discrimination unit 125 distinguishes that it is erroneous activation, the discrimination unit 125 outputs a discrimination result that it is erroneous activation to the transmission unit and outputs log data of acceleration in the traveling direction to the threshold setting unit 126.

The threshold setting unit 126 is connected to the discrimination unit 125. The threshold setting unit 126 retains the first threshold related to the acceleration in the gravity direction (Z direction in FIG. 3) and the second threshold related to the acceleration in the traveling direction (Y direction in FIG. 3).

When initially setting the thresholds for the user, the threshold setting unit 126 acquires the log data of the acceleration in the traveling direction from the discrimination unit 125, and calculates a maximum value P0 of the acceleration in the traveling direction. The threshold setting unit 126 sets the first threshold and the second threshold using the acquired maximum value P0.

For example, the threshold setting unit 126 sets the first threshold A using following Equation 1 (where 0<q<1). The first threshold A is a threshold updated on the basis of the acceleration in the traveling direction (Y direction in FIG. 3) after the initial setting. For example, the coefficient q (also referred to as a first coefficient) is set to approximately 0.5. The first threshold A is set to such an extent as to immediately reacts to a light movement. The first threshold A may be calculated using an equation other than Equation 1 as long as the first threshold A is set to such an extent as to immediately react to a light movement.

$$A = q \times P0 \tag{1}$$

For example, the threshold setting unit 126 sets the second threshold B using following Equation 2 (where 0<q<s<1). The second threshold B is a value larger than the first threshold A and is a threshold fixed after initial setting. For example, the coefficient s (also referred to as a first coefficient) is set to approximately 0.6. The second threshold B is set to be larger than the first threshold A, for example, approximately 2.5 times gravitational acceleration. The second threshold B may be calculated using an equation other than Equation 2 as long as the second threshold B is set to be larger than the first threshold A.

$$B = s \times P0 \tag{2}$$

In the example using Equations 1 and 2, in order to set the second threshold B to a larger value than the first threshold A, the first threshold A and the second threshold B are set using the same value (maximum value P0 of the acceleration in the traveling direction). The first threshold A and the second threshold B may be set using acceleration values in different directions as long as the second threshold B can be set to a larger value than the first threshold A.

When the acceleration in the traveling direction has not exceeded the second threshold in the period until the predetermined discrimination time elapses, the threshold setting unit 126 acquires a log of the acceleration in the traveling direction from the discrimination unit 125. The threshold setting unit 126 performs a state discrimination from characteristics of a waveform of the log data of the acceleration in the traveling direction, and adjusts the threshold on the basis of the distinguished state.

When acquiring the log data of the acceleration in the traveling direction from the discrimination unit 125 in the walking discrimination phase, the threshold setting unit 126 calculates the maximum value of the acceleration in the traveling direction. The threshold setting unit 126 updates the first threshold on the basis of the calculated maximum value. The threshold setting unit 126 outputs the updated first threshold to the discrimination unit 125.

The transmission unit 127 is connected to the discrimination unit 125 and the walking measurement device 13. The transmission unit 127 acquires the discrimination result from the discrimination unit 125. The transmission unit 127 transmits the acquired discrimination result to the walking measurement device 13. For example, when the discrimination result that it is stable walking is transmitted from the transmission unit 127 to the walking measurement device 13, the walking measurement by the walking measurement device 13 is continued. When the discrimination result that walking is stopped or erroneous activation is transmitted from the transmission unit 127 to the walking measurement device 13, the walking measurement by the walking measurement device 13 is stopped.

The configuration of the discrimination device 12 has been described above. Note that the configuration of the discrimination device 12 in FIG. 1 is an example, and the configuration of the discrimination device 12 of the present example embodiment is not limited to the mode as it is.

[Data Acquisition Device]

Figure 4:
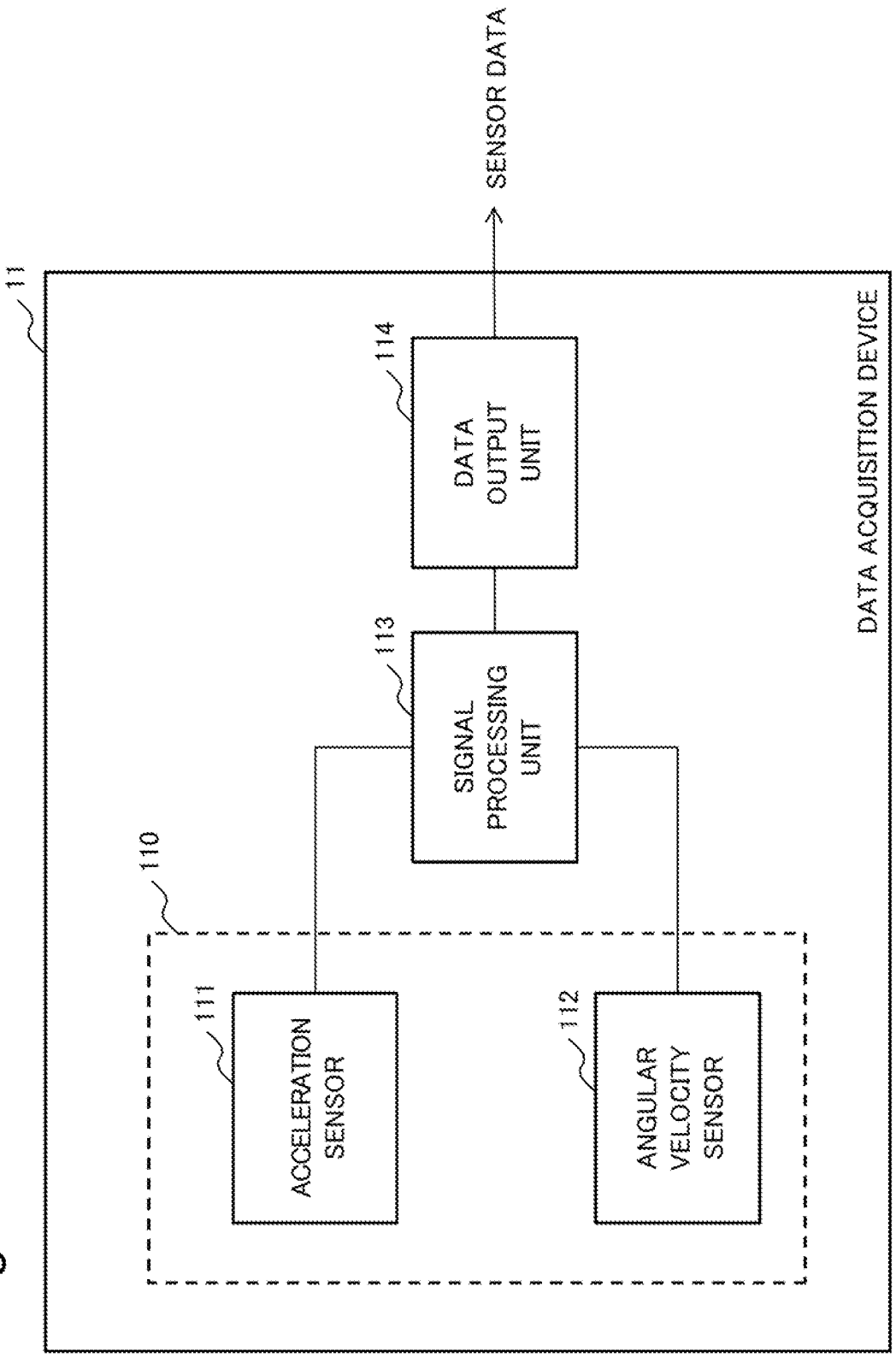
FIG. 4 is a block diagram illustrating a configuration of a data acquisition device of the walking measurement system according to the first example embodiment of the present invention.

Next, the data acquisition device 11 included in the walking measurement system 1 will be described with reference to the drawings. FIG. 4 is a block diagram illustrating an example of a configuration of the data acquisition device 11. The data acquisition device 11 includes an acceleration sensor 111, an angular velocity sensor 112, a signal processing unit 113, and a data output unit 114. The acceleration sensor 111 and the angular velocity sensor 112 constitute a sensor 110. For example, the data acquisition device 11 is implemented by an IMU.

The acceleration sensor 111 is a sensor that measures acceleration in three axial directions. The acceleration sensor 111 outputs the measured acceleration to the signal processing unit 113.

The angular velocity sensor 112 is a sensor that measures an angular velocity. The angular velocity sensor 112 outputs the measured angular velocity to the signal processing unit 113.

The signal processing unit 113 acquires each of the acceleration and the angular velocity from each of the acceleration sensor 111 and the angular velocity sensor 112. The signal processing unit 113 converts the acquired acceleration and angular velocity into digital data, and outputs the digital data (sensor data) after conversion to the data output unit 114. The sensor data includes at least acceleration data obtained by converting acceleration of analog data into digital data and angular velocity data obtained by converting angular velocity of analog data into digital data. The sensor data may include an acquisition time of raw data of acceleration and angular velocity. The signal processing unit may be configured to output sensor data obtained by performing correction such as a mounting error, a temperature correction, and a linearity correction on the acquired raw data of the acceleration and the angular velocity.

The data output unit 114 acquires the sensor data from the signal processing unit 113. The data output unit 114 transmits the acquired sensor data to the discrimination device 12. The data output unit 114 may transmit the sensor data to the discrimination device 12 via a wire such as a cable or a conductive wire, or may transmit the sensor data to the discrimination device 12 via wireless communication. For example, the data output unit 114 can be configured to transmit sensor data to the discrimination device 12 via a wireless communication function (not illustrated) conforming to a standard such as Bluetooth (registered trademark) or WiFi (registered trademark). When the sensor data is directly transmitted from the data output unit 114 to the walking measurement device 13, it is only required to transmit the sensor data from the data output unit 114 to the walking measurement device 13 by wired communication or wireless communication.

The example of the configuration of the data acquisition device 11 has been described above. Note that the configuration of FIG. 4 is an example, and the configuration of the data acquisition device 11 included in the walking measurement system 1 of the present example embodiment is not limited to the mode as it is.

[Operation Mode]

Figure 5:
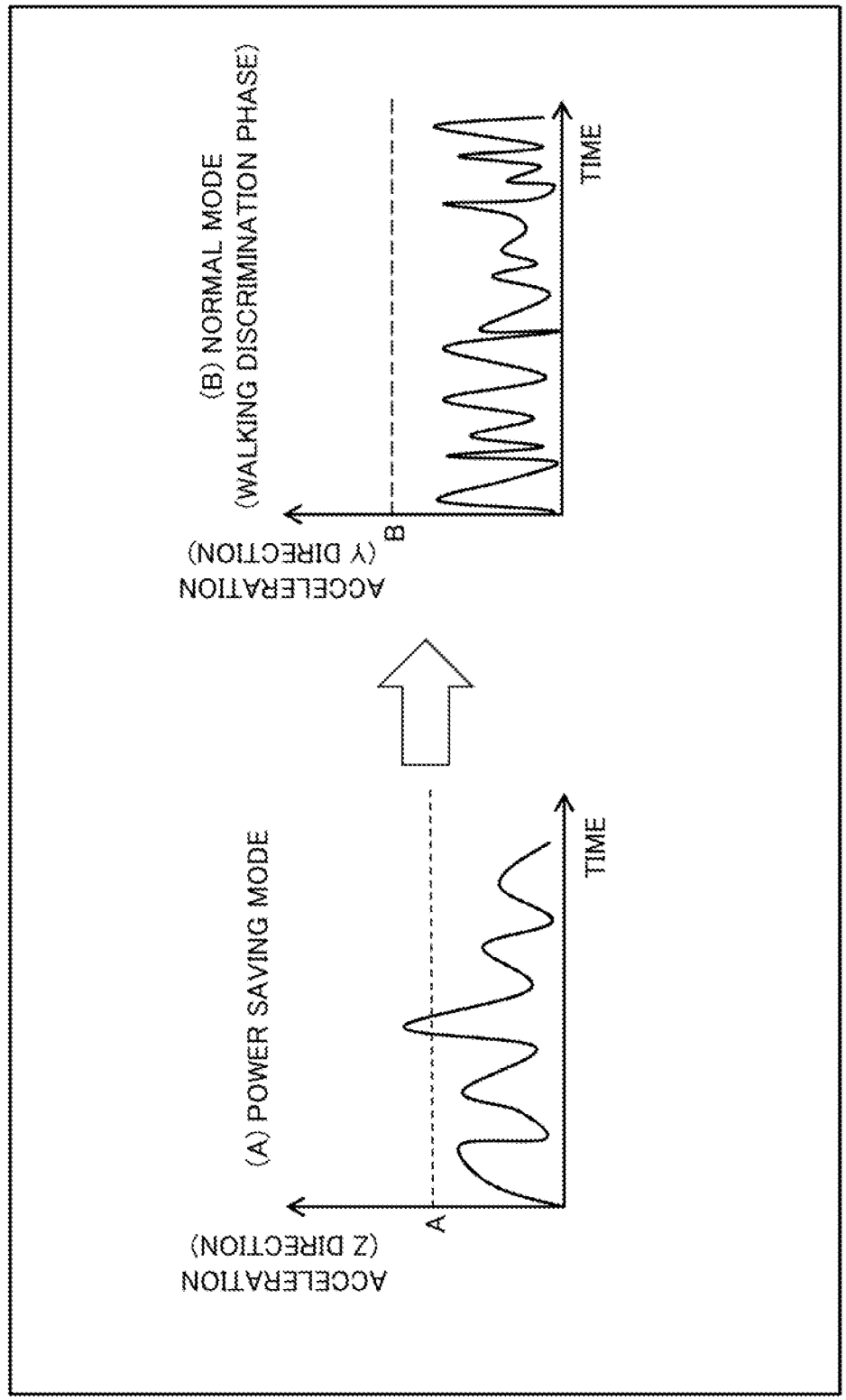
FIG. 5 is a conceptual diagram for illustrating an operation mode of the discrimination device according to the first example embodiment of the present invention.

Next, switching of the operation mode by the discrimination device 12 will be described with reference to the drawings. FIG. 5 is a conceptual diagram for illustrating an example of switching of the operation mode by the discrimination device 12. In the example of FIG. 5, an example is illustrated in which the mode is switched to a normal mode (B) when the discrimination device 12 operating in a power saving mode (A) detects that the acceleration in the gravity direction (Z direction in FIG. 3) has exceeded the first threshold.

At the initial stage of switching to the normal mode (B) (walking discrimination phase), the discrimination device 12 verifies whether the acceleration in the traveling direction (Y direction in FIG. 3) exceeds the second threshold. When the acceleration in the traveling direction has exceeded the second threshold by the prescribed number of times or more within the discrimination time, the discrimination device 12 transmits a discrimination result that it is stable walking to the walking measurement device 13. When the acceleration in the traveling direction has exceeded the second threshold within the discrimination time but has not exceeded the second threshold by the prescribed number of times or more, the discrimination device 12 transmits a discrimination result that walking is stopped to the walking measurement device 13.

The example of FIG. 5 is an example in which the acceleration in the traveling direction has not exceeded the second threshold within the discrimination time. In this case, the discrimination device 12 transmits a discrimination result that it is erroneous activation to the walking measurement device 13 and updates the first threshold.

[Update of First Threshold]

Figure 6:
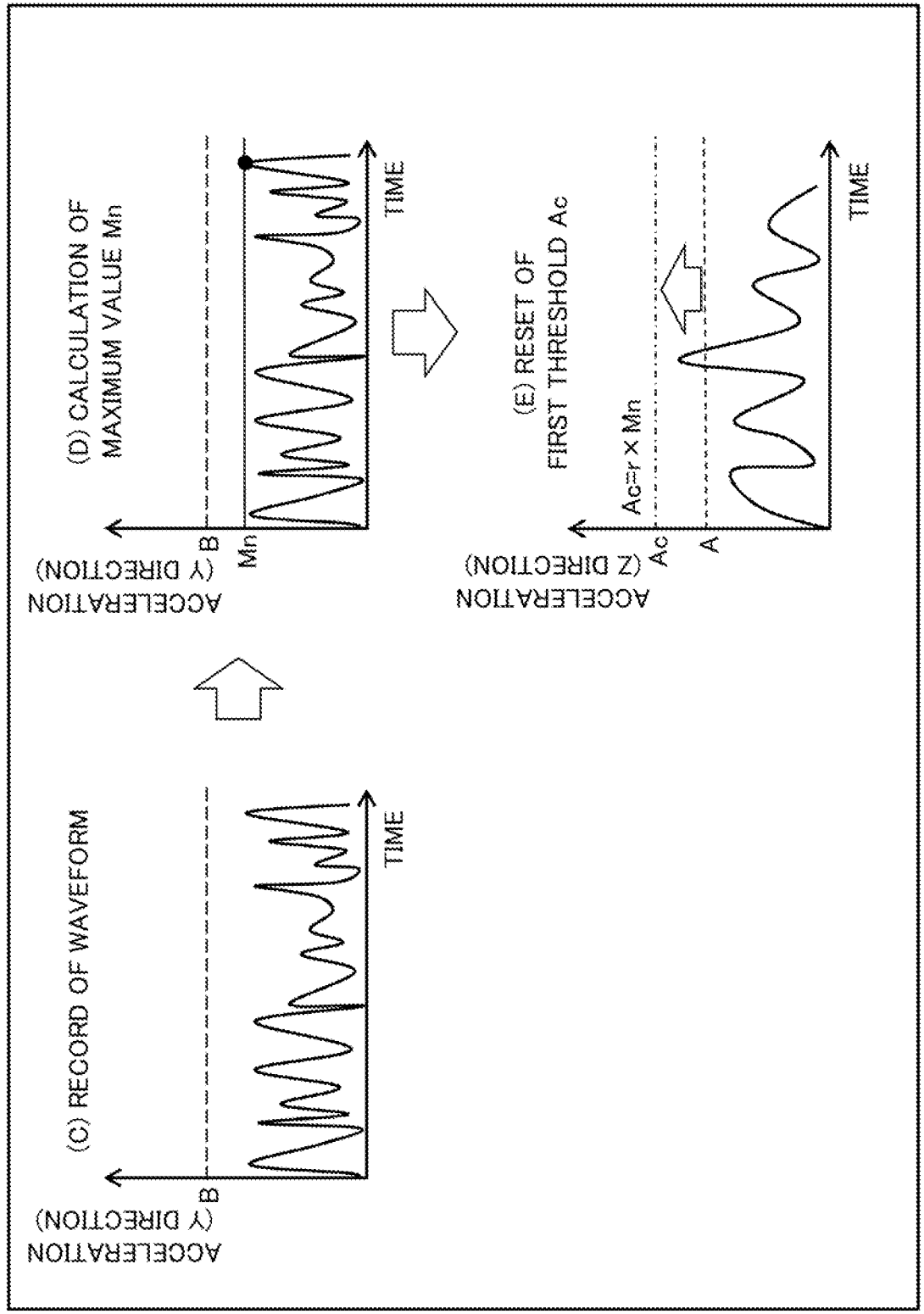
FIG. 6 is a conceptual diagram for illustrating update of a first threshold by the discrimination device according to the first example embodiment of the present invention.

Next, update of the first threshold by the threshold setting unit 126 of the discrimination device 12 will be described with reference to the drawings. FIG. 6 is a conceptual diagram for illustrating an example of update of the first threshold by the threshold setting unit 126. In the example of FIG. 6, a situation is illustrated in which a waveform of the log data of the acceleration in the traveling direction (Y direction in FIG. 3) is recorded (C), a maximum value Mn is calculated from the waveform (D), and the first threshold A is updated to a first threshold Ac on the basis of the calculated maximum value Mn (E).

When acquiring the log data of the acceleration in the traveling direction from the discrimination unit 125, the threshold setting unit 126 calculates the maximum value Mn of the acceleration in the traveling direction. The threshold setting unit 126 updates the first threshold on the basis of the calculated maximum value Mn.

For example, the threshold setting unit 126 updates the first threshold A to the first threshold Ac using following Equation 3. In following Equation 3, the maximum value of the acceleration in the traveling direction is described as Mn, a correction coefficient for updating the first threshold is described as r, and the first threshold after update is described as Ac.

$$Ac = r \times Mn \qquad (3)$$

For example, the correction coefficient r is set to approximately 1.05 to 1.1 in order to increase the first threshold by approximately 5% to 10%. If the correction coefficient r is too small, erroneous activation is not efficiently suppressed and frequently occurs. If the correction coefficient r is too large, the operation mode no longer shifts to the normal mode. Thus, the correction coefficient r is set to an appropriate value that is not too small and not too large. The correction coefficient r may be set to an initial setting value based on the actual measurement value, or may be individually set for each user.

(Operation)

Next, an operation of the walking measurement system 1 of the present example embodiment will be described with reference to the drawings. Hereinafter, description will be started from an example in which the first threshold is initially set for the user. Then, a series of operations will be described in which the walking measurement system 1 detects a start of walking in the low-load power saving mode using acceleration, and performs walking discrimination when switching to the normal mode in which walking measurement is performed using the acceleration and angular velocity.

[Initial Setting]

Figure 7:
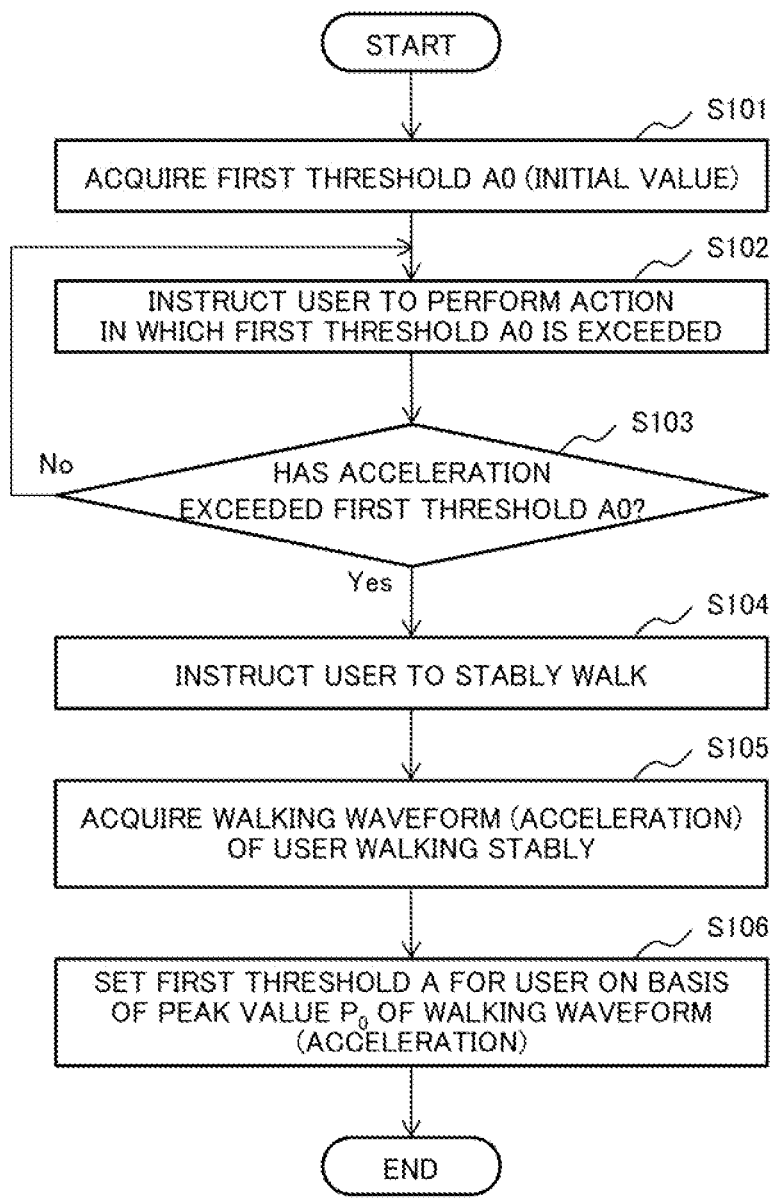
FIG. 7 is a flowchart for illustrating initial setting of the first threshold by the discrimination device according to the first example embodiment of the present invention.

FIG. 7 is a flowchart for illustrating an operation in which the walking measurement system 1 initially sets the first threshold A for the user using an initial value (first threshold A0) of the first threshold. For example, the first threshold A0 is set at the time of production or factory shipment of the walking discrimination device 10. In the example of FIG. 7, it is assumed that an instruction can be issued from the walking measurement system 1 to the user via a display device, a sound device, or the like that is not illustrated. For example, when an application having the function of the walking measurement device 13 is installed in a terminal device such as a smartphone, an instruction can be issued via a display device, a voice device, or the like mounted on the terminal device. In the description along the flowchart of FIG. 7, the walking measurement system 1 will be described as the main body of operation.

In FIG. 7, first, when an initial setting operation is performed by the user, the walking measurement system 1 acquires an initial value (first threshold A0) of the first threshold (step S101). For example, the first threshold A0 is stored in a storage area (not illustrated) of the discrimination device 12 or the walking measurement device 13. The initial setting operation by the user is an operation performed when the user uses the walking measurement system 1 for the first time or when the first threshold is reset.

Next, the walking measurement system 1 instructs the user to perform an action in which the acceleration in the gravity direction (Z direction in FIG. 3) exceeds the first threshold A0 (step S102). For example, the walking measurement system 1 outputs, from the walking measurement device 13, display information and voice information for the user to perform an action in which the acceleration in the gravity direction exceeds the first threshold A0.

Here, when the acceleration in the gravity direction has exceeded the first threshold A0 (Yes in step S103), the walking measurement system 1 instructs the user to perform stable walking (step S104). For example, the walking measurement system 1 outputs display information and voice information for the user to perform stable walking from the walking measurement device 13. On the other hand, when the acceleration in the gravity direction has not exceeded the first threshold A0 (No in step S103), the processing returns to step S102.

Next, the walking measurement system 1 acquires a walking waveform obtained by stable walking performed by the user (step S105). At this time, the walking measurement system 1 acquires a walking waveform of the acceleration in the traveling direction (Y direction in FIG. 3).

Next, the walking measurement system 1 sets a first threshold A for the user on the basis of the acquired peak value of the walking waveform (step S106). The walking measurement system 1 causes the threshold setting unit 126 of the discrimination device 12 to store the first threshold A.

The operation in which the walking measurement system 1 initializes the first threshold A for the user using the first threshold A0 has been described above. Note that the flowchart of FIG. 7 is an example, and the operation of initial setting of the first threshold A by the walking measurement system 1 of the present example embodiment is not limited to the procedure as it is.

[Switching of Operation Mode]

Figure 8:
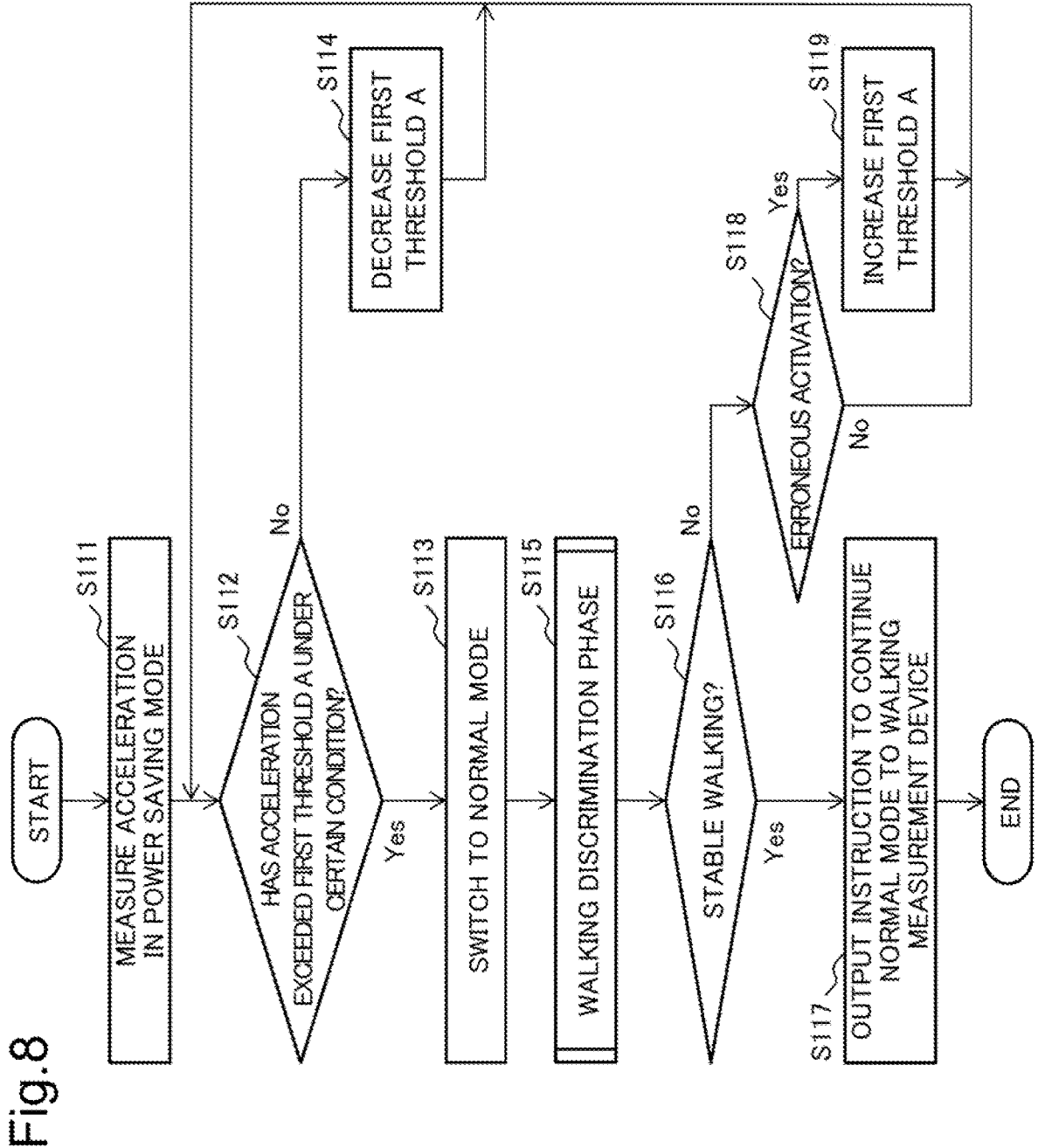
FIG. 8 is a flowchart for illustrating an operation of the discrimination device according to the first example embodiment of the present invention.

FIG. 8 is a flowchart for illustrating an example of switching the operation mode from the power saving mode to the normal mode according to an operation of the user. In the description along the flowchart of FIG. 8, the discrimination device 12 will be described as the main body of operation.

In FIG. 8, first, the discrimination device 12 measures acceleration in the power saving mode (step S111).

When the acceleration in the gravity direction (Z direction in FIG. 3) exceeds the first threshold A under a certain condition (Yes in step S112), the discrimination device 12 switches the operation mode to the normal mode (step S113).

On the other hand, when the acceleration in the gravity direction has not exceeded the first threshold A under the certain condition (No in step S112), the discrimination device 12 decreases the value of the first threshold A (step S114). After step S114, the processing returns to step S112. For example, in step S114, the value of the first threshold A is returned to the value at the time of the previous normal activation. In step S114, the value of the first threshold A may be decreased by a predetermined value.

After step S113, the discrimination device 12 shifts to the walking discrimination phase and distinguishes the walking state (step S115). In the walking discrimination phase (step S115), the discrimination device 12 distinguishes whether the walking state of the user is stable walking, stop of walking, or erroneous activation.

When the discrimination result is stable walking (Yes in step S116), the discrimination device 12 outputs an instruction to continue the normal mode to the walking measurement device 13 (step S117). In step S117, the walking discrimination phase of FIG. 8 ends. The walking discrimination phase in FIG. 8 may be stopped at a stage when the power saving mode is switched to the normal mode, may be periodically executed, or may be continued as it is. On the other hand, when the discrimination result is not stable walking (No in step S116), the discrimination device 12 executes different processing depending on whether it is erroneous activation (step S118).

When it is erroneous activation (Yes in step S118), the discrimination device 12 increases the value of the first threshold A (step S119). After step S119, the processing returns to step S112. On the other hand, when it is not erroneous activation (No in step S118), the discrimination device 12 returns to step S112 without updating the value of the first threshold A. After step S118 or step S119, the walking measurement device 13 may be configured to be notified of stop walking or erroneous activation. When the walking measurement device 13 is notified of stop of walking or erroneous activation, it is only required to transmit an instruction to stop the normal mode to the walking measurement device 13.

The example of switching the operation mode from the power saving mode to the normal mode according to the operation of the user has been described above. Note that the flowchart of FIG. 8 is an example, and the switching of the operation mode from the power saving mode to the normal mode by the discrimination device 12 of the present example embodiment is not limited to the procedure as it is.

[Walking Discrimination Phase]

Figure 9:
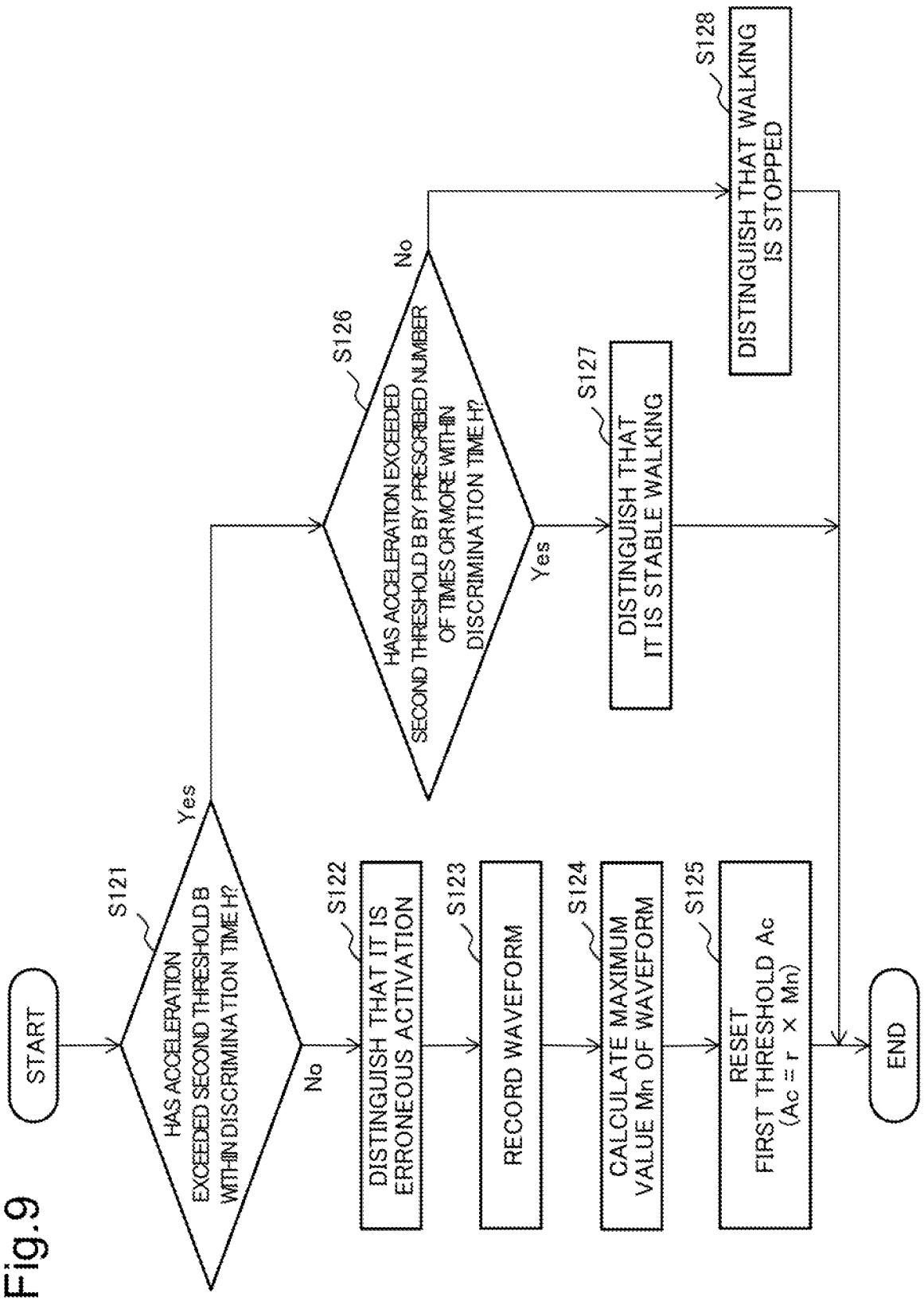
FIG. 9 is a flowchart for illustrating a walking discrimination phase by the discrimination device according to the first example embodiment of the present invention.

FIG. 9 is a flowchart for illustrating an operation in the walking discrimination phase executed when the operation mode is switched from the power saving mode to the normal mode. In the description along the flowchart of FIG. 9, the discrimination device 12 will be described as the main body of operation.

In FIG. 9, first, the discrimination device 12 distinguishes whether the acceleration in the traveling direction (Y direction in FIG. 3) has exceeded the second threshold B within a discrimination time H (step S121).

When the acceleration in the traveling direction has not exceeded the second threshold B within the discrimination time H (No in step S121), the discrimination device 12 distinguishes that it is erroneous activation (step S122), and records the waveform of the acceleration in the traveling direction (step S123). Next, the discrimination device 12 calculates the maximum value Mn of the waveform of the acceleration in the traveling direction (step S124). Then, the discrimination device 12 resets the first threshold Ac by applying the calculated maximum value Mn to above Equation 3 (step S125). After step S125, the processing proceeds to step S116 in FIG. 8.

On the other hand, when the acceleration in the traveling direction has exceeded the second threshold B within the discrimination time H (Yes in step S121), the discrimination device 12 distinguishes whether the acceleration in the traveling direction has exceeded the second threshold B by a prescribed number of times or more within the discrimination time H (step S126).

When the acceleration in the traveling direction has exceeded the second threshold B by the prescribed number of times or more within the discrimination time H (Yes in step S126), the discrimination device 12 distinguishes that it is stable walking (step S127). On the other hand, when the acceleration in the traveling direction has not exceeded the second threshold B by the prescribed number of times or more within the discrimination time H (No in step S126), the discrimination device 12 distinguishes that walking is stopped (step S128). After steps S127 and S128, the processing proceeds to step S116 in FIG. 8.

The operation in the walking discrimination phase has been described above. Note that the processing along the flowchart of FIG. 9 is an example, and the operation in the walking discrimination phase by the discrimination device 12 is not limited to the procedure as it is.

As described above, the walking measurement system of the present example embodiment includes a data acquisition device, a discrimination device, and a walking measurement device. The data acquisition device according to one aspect of the present example embodiment is placed in a shoe, detects acceleration and angular velocity, generates sensor data including the detected acceleration and angular velocity, and transmits the generated sensor data to the discrimination device. The walking measurement device according to one aspect of the present example embodiment acquires the sensor data generated by the data acquisition device and a discrimination result from the discrimination device, is activated and stopped according to the discrimination result, and measures walking using the sensor data.

The discrimination device according to one aspect of the present example embodiment includes a log acquisition unit, a storage unit, a call unit, a discrimination unit, a threshold setting unit, and a transmission unit. The log acquisition unit acquires sensor data including acceleration acquired by a sensor placed in a shoe. The storage unit stores log data of the sensor data acquired by the log acquisition unit. The log calling unit calls the log data stored in the storage unit. The discrimination unit distinguishes a walking state from a waveform of the log data called by the log calling unit. When acceleration included in the log data has not exceeded a second threshold within a discrimination time, the discrimination unit outputs a discrimination result that it is erroneous activation. The threshold setting unit retains a first threshold related to acceleration in a gravity direction and the second threshold related to acceleration in a traveling direction, and sets the first threshold and the second threshold on the basis of a discrimination result by the discrimination unit. The threshold setting unit updates the first threshold based on a value of the acceleration in the traveling direction included in the log data according to the discrimination result that it is erroneous activation. The transmission unit transmits the discrimination result by the discrimination unit.

In one aspect of the present example embodiment, the threshold setting unit sets, as the first threshold, a value obtained by multiplying a maximum value of the acceleration in the traveling direction included in the log data by a correction coefficient according to the discrimination result that it is erroneous activation.

In one aspect of the present example embodiment, when the acceleration included in the log data has exceeded the second threshold by a prescribed number of times or more within a discrimination time, the discrimination unit outputs the discrimination result that it is stable walking. On the other hand, when the acceleration included in the log data has not exceeded the second threshold by the prescribed number of times or more within the discrimination time, the discrimination unit outputs a discrimination result that walking is stopped.

In one aspect of the present example embodiment, when the acceleration included in the log data has not exceeded the first threshold under a certain condition, the discrimination unit outputs an instruction to decrease the first threshold to the threshold setting unit. The threshold setting unit decreases the first threshold in response to the instruction to decrease the first threshold by the discrimination unit. For example, the threshold setting unit sets, in response to the instruction to decrease the first threshold by the discrimination unit, the first threshold to a value of the first threshold when it has been previously distinguished that it is stable walking.

In one aspect of the present example embodiment, the threshold setting unit acquires, at a time of initial setting, the log data of the sensor data acquired by the sensor installed in the shoe of the user performing stable walking. The threshold setting unit sets a value obtained by multiplying a maximum value of the acceleration in the traveling direction by a first coefficient as the first threshold, and sets a value obtained by multiplying a second coefficient smaller than the first coefficient by the maximum value of the acceleration in the traveling direction as the second threshold.

The walking measurement system of the present example embodiment can flexibly set the threshold for switching the operation mode on the basis of the log data of the sensor data. In particular, the walking measurement system of the present example embodiment flexibly sets the first threshold of the acceleration in the gravity direction on the basis of the acceleration in the traveling direction. Thus, with the walking measurement system of the present example embodiment, it is possible to achieve high efficiency and low power consumption of walking measurement while flexibly responding to changes in a walking state.

(Hardware)

Here, a hardware configuration for executing the processing of the walking measurement device according to the first example embodiment of the present invention will be described using the information processing device 90 of FIG. 10 as an example. Note that the information processing device 90 in FIG. 10 is a configuration example for executing the processing of the walking measurement device of the first example embodiment, and does not limit the scope of the present invention.

Figure 10:
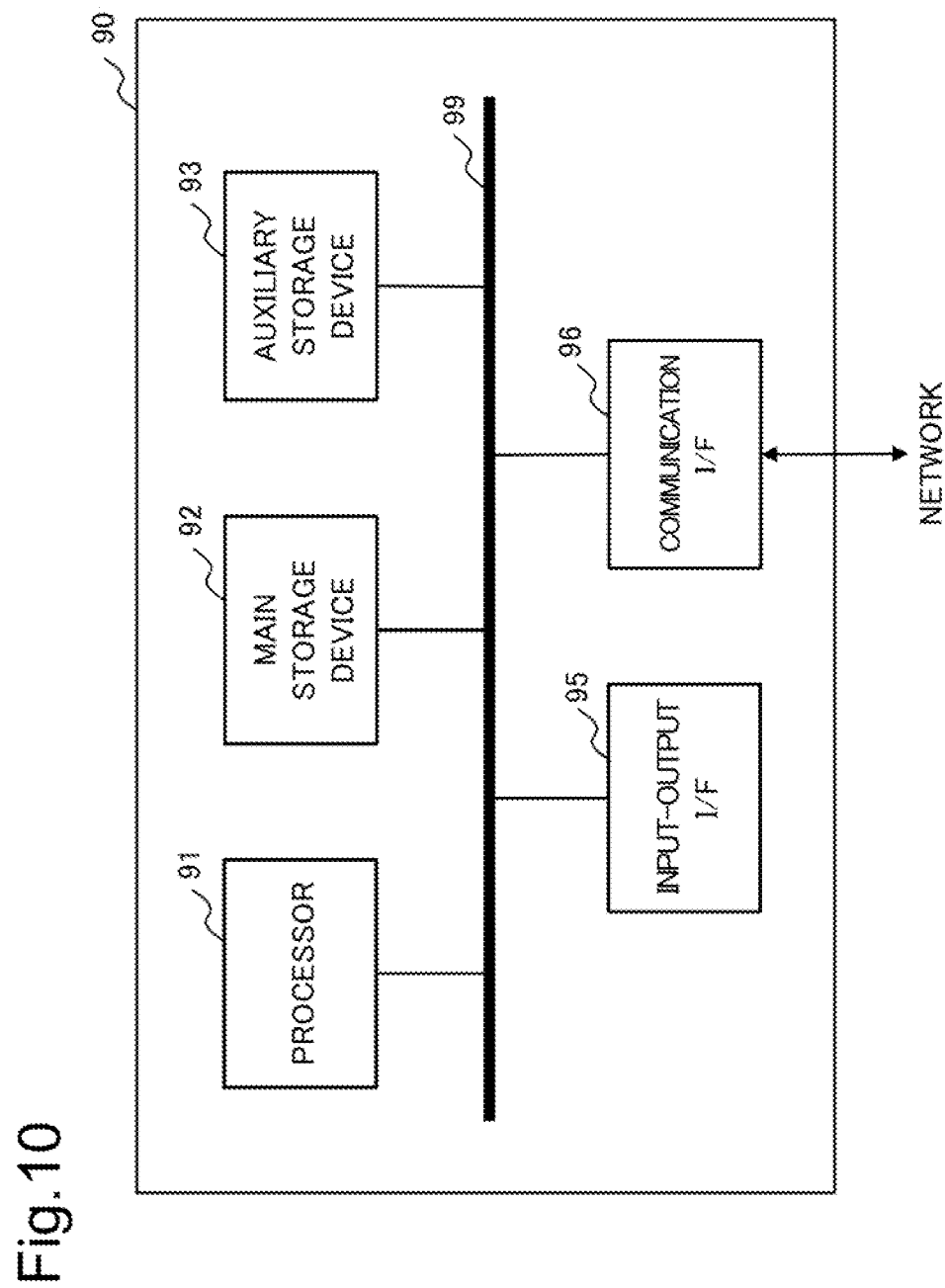
FIG. 10 is a conceptual diagram illustrating a hardware configuration for achieving the discrimination device and the walking measurement device according to the first example embodiment of the present invention.

As illustrated in FIG. 10, the information processing device 90 includes a processor 91, a main storage device 92, an auxiliary storage device 93, an input-output interface 95, and a communication interface 96. In FIG. 10, the interface is abbreviated as I/F. The processor 91, the main storage device 92, the auxiliary storage device 93, the input-output interface 95, and the communication interface 96 are data-communicably connected to each other via a bus 99. The processor 91, the main storage device 92, the auxiliary storage device 93, and the input-output interface 95 are connected to a network such as the Internet or an intranet via the communication interface 96.

The processor 91 develops a program stored in the auxiliary storage device 93 or the like in the main storage device 92 and executes the developed program. In the present example embodiment, it is only required to use a software program installed in the information processing device 90. The processor 91 executes processing by the walking measurement device according to the present example embodiment.

The main storage device 92 has an area in which a program is developed. The main storage device 92 is only required to be, for example, a volatile memory such as a dynamic random access memory (DRAM). A nonvolatile memory such as a magnetoresistive random access memory (MRAM) may be configured and added as the main storage device 92.

The auxiliary storage device 93 stores various data. The auxiliary storage device 93 includes a local disk such as a hard disk or a flash memory. In addition, the main storage device 92 may be configured to store various data, and the auxiliary storage device 93 may be omitted.

The input-output interface 95 is an interface for connecting the information processing device 90 and a peripheral device. The communication interface 96 is an interface for connecting to an external system or device through a network such as the Internet or an intranet on the basis of a standard or a description. The input-output interface 95 and the communication interface 96 may be shared as an interface connected to an external device.

An input device such as a keyboard, a mouse, or a touch panel may be connected to the information processing device 90 as necessary. These input devices are used to input information and settings. When the touch panel is used as the input device, the display screen of the display device is only required to also serve as the interface of the input device. Data communication between the processor 91 and the input device is only required to be mediated by the input-output interface 95.

The information processing device 90 may be provided with a display device for displaying information. When a display device is provided, the information processing device 90 preferably includes a display control device (not illustrated) for controlling display of the display device. The display device is only required to be connected to the information processing device 90 via the input-output interface 95.

The information processing device 90 may be provided with a disk drive as necessary. The disk drive is connected to the bus 99. The disk drive mediates reading of data and/or program from a recording medium, writing of a processing result of the information processing device 90 to the recording medium, and the like between the processor 91 and the recording medium (program recording medium), which is not illustrated. The recording medium can be achieved by, for example, an optical recording medium such as a compact disc (CD) or a digital versatile disc (DVD). The recording medium may be achieved by a semiconductor recording medium such as a universal serial bus (USB) memory or a secure digital (SD) card, a magnetic recording medium such as a flexible disk, or another recording medium.

The above is an example of a hardware configuration for enabling the walking measurement device according to the first example embodiment of the present invention. Note that the hardware configuration of FIG. 10 is an example of a hardware configuration for executing arithmetic processing of the walking measurement device according to the first example embodiment, and does not limit the scope of the present invention. A program for causing a computer to execute processing related to the walking measurement device according to the first example embodiment is also included in the scope of the present invention. Further, a program recording medium in which the program according to the first example embodiment is recorded is also included in the scope of the present invention.

The components of the walking measurement device of the first example embodiment can be freely combined. The components of the walking measurement device of the first example embodiment may be achieved by software or may be achieved by a circuit.

While the present invention has been particularly shown and described with reference to example embodiments thereof, the invention is not limited to these embodiments. It will be understood by those of ordinary skill in the art that various changes in form and details may be made therein without departing from the spirit and scope of the present invention as defined by the claims.

REFERENCE SIGNS LIST

1 Walking measurement system
10 Walking discrimination device
11 Data acquisition device
12 Discrimination device
13 Walking measurement device
110 Sensor
111 Acceleration sensor
112 Angular velocity sensor
113 Signal processing unit
114 Data output unit
121 Log acquisition unit
122 Storage unit
123 Log calling unit
125 Discrimination unit
126 Threshold setting unit
127 Transmission unit

What is claimed is:

1. A discrimination device comprising:
a microcomputer comprising instructions configured to control the microcomputer to:
acquire sensor data including acceleration acquired by a sensor;
store log data of the sensor data that has been acquired in a storage;
control the sensor to increase an acquisition frequency of the sensor data in response to acceleration in a gravity direction included in the sensor data exceeding a first threshold related to the acceleration in a gravity direction according to an operation of a user;
call the log data stored in the storage;
distinguish a walking state from among stable walking, stop of walking, and erroneous activation according to the number of times that acceleration in a traveling direction included in the log data that has been called exceeds a second threshold related to the acceleration in a traveling direction within a determination time;
retain the first threshold related to the acceleration in the gravity direction and the second threshold related to the acceleration in the traveling direction,
set the first threshold and the second threshold based on a discrimination result; and
transmit the discrimination result, wherein the instructions are further computer to control the microcomputer to output a discrimination result indicating erroneous activation, when acceleration included in the log data has not exceeded the second threshold within the discrimination time, and update the first threshold based on a value of the acceleration in the traveling direction included in the log data according to the discrimination result indicating erroneous activation.

2. The discrimination device according to claim 1, wherein the instructions are further computer to control the microcomputer to set, as the first threshold, a value obtained by multiplying a maximum value of the acceleration in the traveling direction included in the log data by a correction coefficient according to the discrimination result indicating erroneous activation.

3. The discrimination device according to claim 1, wherein the instructions are further computer to control the microcomputer to output the discrimination result indicating stable walking when the acceleration included in the log data has exceeded the second threshold by a prescribed number of times or more within a discrimination time, and output the discrimination result that walking is stopped when the acceleration included in the log data has not exceeded the second threshold by the prescribed number of times or more within the discrimination time.

4. The discrimination device according to claim 1, wherein the instructions are further computer to control the microcomputer to generate an instruction to decrease the first threshold when the acceleration included in the log data has not exceeded the first threshold under a certain condition, and decrease the first threshold in response to the instruction to decrease the first threshold.

5. The discrimination device according to claim 4, wherein the instructions are further computer to control the microcomputer to set, in response to the instruction to decrease the first threshold, the first threshold to a value of the first threshold when the discrimination result indicates stable walking.

6. The discrimination device according to claim 1, wherein the instructions are further computer to control the microcomputer to acquire, at a time of initial setting, the log data of the sensor data acquired by the sensor of the user performing stable walking, set a value obtained by multiplying a maximum value of the acceleration in the traveling direction by a first coefficient as the first threshold, and set a value obtained by multiplying a second coefficient smaller than the first coefficient by the maximum value of the acceleration in the traveling direction as the second threshold.

7. A walking measurement system comprising:
the discrimination device according to claim 1; and
a data acquisition device that comprises the sensor, wherein the sensor is configured to measure acceleration and angular velocity, generates sensor data including the detected acceleration and angular velocity, and transmit the generated sensor data to the discrimination device.

8. The walking measurement system according to claim 7, wherein the instructions are further computer to control the microcomputer to provide a walking measurement device with the sensor data generated by the data acquisition device and the discrimination result from the discrimination device, and to activate and stop the walking measurement device according to the discrimination result.

9. A discrimination method comprising:
acquiring sensor data including acceleration acquired by a sensor;
storing log data of the acquired sensor data in a storage;
controlling the sensor to increase an acquisition frequency of the sensor data in response to acceleration in a gravity direction included in the sensor data exceeding a first threshold related to the acceleration in a gravity direction according to an operation of a user;
calling the log data stored in the storage;
distinguishing a walking state from among stable walking, stop of walking, and erroneous activation according to the number of times that acceleration in a traveling direction included in the called log data exceeds a second threshold related to the acceleration in a traveling direction within a determination time;
setting the first threshold related to the acceleration in the gravity direction and the second threshold related to the acceleration in the traveling direction based on a discrimination result of the walking state;
outputting a discrimination result indicating erroneous activation when acceleration included in the log data has not exceeded the second threshold within the discrimination time; and
updating the first threshold based on a value of the acceleration in the traveling direction included in the log data according to the discrimination result indicating erroneous activation.

10. A non-transient program recording medium recording a program that causes a computer to execute processing comprising:
acquiring sensor data including acceleration acquired by a sensor;
storing the log data of the acquired sensor data in a storage;
controlling the sensor to increase an acquisition frequency of the sensor data in response to acceleration in a gravity direction included in the sensor data exceeding a first threshold related to the acceleration in a gravity direction according to an operation of a user;
calling the log data stored in the storage;
distinguishing a walking state from among stable walking, stop of walking, and erroneous activation according to the number of times that acceleration in a traveling direction included in the called log data exceeds a second threshold related to the acceleration in a traveling direction within a determination time;
setting the first threshold related to the acceleration in the gravity direction and the second threshold related to the acceleration in the traveling direction based on a discrimination result of the walking state;
outputting a discrimination result indicating erroneous activation when acceleration included in the log data has not exceeded the second threshold within the discrimination time; and updating the first threshold based on a value of the acceleration in the traveling direction included in the log data according to the discrimination result indicating erroneous activation.

* * * * *